United States Patent [19]
Kurtzberg et al.

[11] Patent Number: 5,586,049
[45] Date of Patent: Dec. 17, 1996

[54] APPARATUS AND METHOD FOR GENERATING PROFILES OF CONSTITUENTS OF CHEMICAL MIXTURES

[75] Inventors: Jerome M. Kurtzberg, Yorktown Heights; John S. Lew, Ossining, both of N.Y.

[73] Assignee: International Business Machines Corporation, Armonk, N.Y.

[21] Appl. No.: 325,858

[22] Filed: Oct. 19, 1994

[51] Int. Cl.$^6$ .................................................. G01N 21/31
[52] U.S. Cl. .................. 364/499; 364/498; 364/496; 364/525; 324/307; 73/23.37; 210/745
[58] Field of Search .................................. 364/496, 497, 364/498, 300, 550, 577, 525, 499; 73/23.36, 23.37; 356/300, 334, 318, 319; 436/171; 324/307; 210/745, 656

[56] References Cited

U.S. PATENT DOCUMENTS

| | | |
|---|---|---|
| 4,807,148 | 2/1989 | Lacey ........................... 364/498 |
| 4,847,792 | 7/1989 | Barna et al. ................... 364/552 |
| 4,885,254 | 12/1989 | Sung ............................... 436/85 |
| 4,986,658 | 1/1991 | Kim ........................ 356/318 OR |
| 5,014,217 | 5/1991 | Savage ........................... 364/498 |
| 5,023,804 | 6/1991 | Hoult .............................. 364/498 |
| 5,046,846 | 9/1991 | Ray et al. .................... 364/498 X |
| 5,121,337 | 6/1992 | Brown ............................ 364/498 |
| 5,121,338 | 6/1992 | Lodder ............................ 364/498 |
| 5,124,932 | 6/1992 | Lodder ............................ 364/498 |
| 5,218,299 | 6/1993 | Dunkel ..................... 324/307 OR |
| 5,242,602 | 9/1993 | Richardson et al. ............ 364/600 |

OTHER PUBLICATIONS

Alexopoulos, C.; Distribution–free Confidence Intervals for Conditional Probabilities and Ratios of Expections; Management Science, vol. 41, No. 12, pp. 1748–1763.

Federgruen, A. et al., A simple forward algorithm to solve general dynamic lot sizing models with n periods in O(n log n) or O(n) time; The Institute of Management Science, vol. 37, No. 8, pp. 909–925.

*Primary Examiner*—James P. Trammell
*Assistant Examiner*—Kamini Shah
*Attorney, Agent, or Firm*—Daniel P. Morris

[57] ABSTRACT

An apparatus, system and method are described for determining profiles of the absolute or relative concentrations of N constituent chemical components of a chemical mixture over a group of samples. For each sample a plurality of sets of concentrations is determined wherein each set has substantially the same error for corresponding to the absorption spectra measured for the composite sample. A plurality of samples of the chemical mixture are generated, for example, by removing parts of a surface sequentially. From amongst the plurality of sets of absolute or relative concentrations over the plurality of samples, a path of highest probability is determined from which profiles of each of the chemical components can be determined. The invention is applied to generating profiles of chemical constituents as material is received from a surface of a semiconductor chip to generate profiles as a function of depth into the sample.

37 Claims, 6 Drawing Sheets

APPARATUS AND METHOD FOR GENERATING PROFILES OF CONSTITUENTS OF CHEMICAL MIXTURES

CROSS REFERENCE TO RELATE APPLICATIONS

U.S. application Ser. No. 08/325,746 filed on the same day herewith entitled "Error Minimization Apparatus and Method for Real-Time Spectral Deconvolution of Chemical Mixtures" to J. Kurtzberg et al., the teaching of which is incorporated herein by reference, describes an apparatus, system, and method for determining the quantities or relative concentrations of N constituent chemical components of a chemical nature. The spectral response, $C_i$, of a composite sample is measured at M wavelengths $\lambda_i$, wherein $M \geq N$. For the jth constituent, $X_j$ is the absolute quantity, or the relative concentration when the mixture has known total mass, while $A_{ij}$ is the spectral response of the jth component at wavelength $\lambda_i$. The set of M equations $$\sum_{j=1}^{N} A_{i,j} X_m = C_i$$

have intersections defining values of $X_j$ of which only those within the region defined by $0 \leq X_j$ are possible values of $X_j$. An error is assigned to each intersection and the intersection of minimum error defines the values of $X_j$. Such a determination is rapid. A profile of each of the quantities or relative concentrations $X_j$ in the sample is readily and rapidly determined.

U.S. application Ser. No. 08/326,101 filed on the same day herewith entitled "Apparatus and Method for Real-Time Spectral Deconvolution of Chemical Mixtures" to J. Kurtzberg et al., the teaching of which is incorporated herein by reference describes an apparatus, system, and method for determining the quantities or relative concentrations of the constituent chemical components of a chemical mixture. The spectral response of the composite sample, measured at a number of wavelengths $\lambda_i$, represented by a vector C. For the jth constituent, $X_j$ is the absolute quantity, or relative concentration when the mixture has known total mass; and the quantities or relative concentrations of each of the chemical constituents are represented by the vector X. The vector X can be determined from the vector C by the following matrix equation: $X=(A^TA)^{-1}A^TC$ wherein the matrix A has elements $A_{ij}$, which is the spectral response of the jth component at wavelength $\lambda_i$. Since the matrix A is a predetermined set of numbers, the elements of vector X are readily determined from the above equation. Such a determination is rapid; a profile of each of the constituents $X_j$ in the sample is readily and rapidly determined.

FIELD OF THE INVENTION

The present invention is directed to a method, system, and apparatus for generating profiles of constituents in chemical mixtures, in particular selecting a profile of highest probability from among a number of choices of possible profiles.

BACKGROUND OF THE INVENTION

Contemporary technology offers many instances that require rapidly identifying the constituents of a chemical mixture. The chemical mixture can be a solid, a liquid or a gas. In the semiconductor industry numerous multilayered structures are made, for example on semiconductor chips or semiconductor chip packaging substrates. In order to monitor the quality of the products being fabricated, it may be necessary to determine the profile of various chemical species in the multilayer structure. This can be done by ablating away the material from the surface and analyzing the material that is ablated away. For such a process to have practical value, it is imperative that the ablating or etching away of the material be done rapidly and that the analysis of the etched or ablated material be performed rapidly.

In the case of a chemical fabrication process for a liquid, it may be desirable to monitor continually the constituent components of the liquid formed by the process. For such monitoring to have value in practical use, it is imperative that the analysis of the liquid be done rapidly so that, as the liquid flows past the monitoring point, an analysis can be done at a closely spaced sequence of times.

As another example, in order to comply with increasingly stringent environmental standards it may be necessary to reduce pollutants emitted into the atmosphere by smokestacks of a manufacturing facility. To do this it may be necessary to monitor continually the chemical constituents of the gases emitted by a smokestack. To do this efficiently it may be necessary to determine these constituents at closely spaced times.

As another example, it may be desirable to construct apparatus that can be controlled so that it runs at peak efficiency, an illustrative example being a gasoline engine. To maximize the efficiency of such an engine, and minimize the pollutants in its exhaust emissions, it may become imperative to monitor continually the chemical constituents in the exhaust from the engine, and the chemical constituents of the fuel entering the engine, so that a feedback control mechanism from the exhaust monitoring can achieve the stated goals. Such an engine would require continually monitoring, at closely spaced intervals of time, the chemical constituents of the exhaust and of the fuel input.

U.S. Pat. No. 2,866,899 to Busignies et al. describes an electronic spectroanalysis computer. The apparatus quantitatively analyzes an infrared absorption spectrum of a multicomponent sample to provide a quantitative deconvolution, i.e., a decomposition of the complex spectrum in terms of the constituents' spectra. The technique involves integrations; these integrations are time-consuming and therefore inefficient.

It is an object of the present invention to provide a system, method, and apparatus for providing profiles of the quantity or relative concentration of chemical constituents of a composite sample, and for doing this with minimal computation time.

It is a further object of the present invention to provide a system, method, and apparatus for determining said quantities or concentrations, and providing profiles of them, when the values $A_{ij}$ admit multiple possibilities.

SUMMARY OF THE INVENTION

A broad aspect of the invention is an apparatus for determining the most probable profile for quantities or relative concentrations of component chemical constituents in a chemical mixture over a plurality of ordered samples of the chemical mixture wherein there is at least one set of quantities or relative concentrations for each of the samples. The apparatus includes: a means for assigning unit probability to each of the sets of quantities or relative concentrations for an initial one of the samples; a means for assigning a transition probability of a transition from each of the sets of one of the ordered samples to each of the sets on the next ordered sample; a means for accumulating the transition probability assigned to each of the sets including the transition probabilities of all transitions from a set in the initial sample; and a means for choosing, for each of the sets having more than one of the transitions, the transition resulting in the highest probability for the set and discarding all other transitions.

Another broad aspect of the invention is a method for determining the most probable profile for quantities or relative concentrations of component chemical constituents in a chemical mixture over a plurality of ordered samples of the chemical mixture wherein there is at least one set of quantities or relative concentrations for each of the samples. The method includes the steps of: assigning unit probability to each of the sets of relative concentrations for an initial one of samples; assigning a transition probability of a transition from each of the sets of one of the ordered samples to each of the sets on the next ordered sample; accumulating the transition probability assigned to each of the sets including the transition probabilities of all transitions From a set in the initial sample; and choosing, for each of the sets having more than one of the transitions, the transition resulting in the highest probability for the set and discarding all other transitions.

BRIEF DESCRIPTION OF THE DRAWINGS

These and other objects, features and advantages of the present invention will become apparent upon consideration of the following detailed description of the invention when read in conjunction with the drawings and figures, in which.

DETAILED DESCRIPTION

For the purpose of easily understanding the details of the present invention, it is described in terms of analyzing the chemical constituents of a semiconductor wafer. This is exemplary only and not limiting. The process of forming a semiconductor wafer on which integrated circuits are formed is well known. In such processing, the wafers are exposed to a sequence of chemical steps, heat treatments and mechanical operations. During this processing, it is generally known, from knowledge of the chemistry, what types of chemical compounds are included in the semiconductor wafer as each layer of an integrated circuit is formed. This knowledge can come from information about the chemicals which are being deposited as well as from understanding of the chemical reactions occurring at a surface, reactions which may form other chemical compounds. Thus, from this knowledge of the base processing of the semiconductor wafer, it is known that, in this wafer, there is a set of N possible chemical component constituents. In order to diagnose problems associated with the fabrication process for a semiconductor wafer, it is desirable to monitor the fabrication process so as to analyze the wafer, i.e., to determine the actual profile of each of the N chemical component constituents from the surface of the fully fabricated semiconductor device down to a depth into the substrate.

The apparatus described herein constitutes an apparatus in which such a semiconductor wafer can be placed, and in which there is a means to remove material, in sequence of time, from the surface of the substrate. The removed material is exposed with radiation and the absorption spectrum is measured. The apparatus, according to the present invention, provides a means for determining the relative concentrations of each of the N component chemical constituents contained in the sample being measured.

Figure 1:
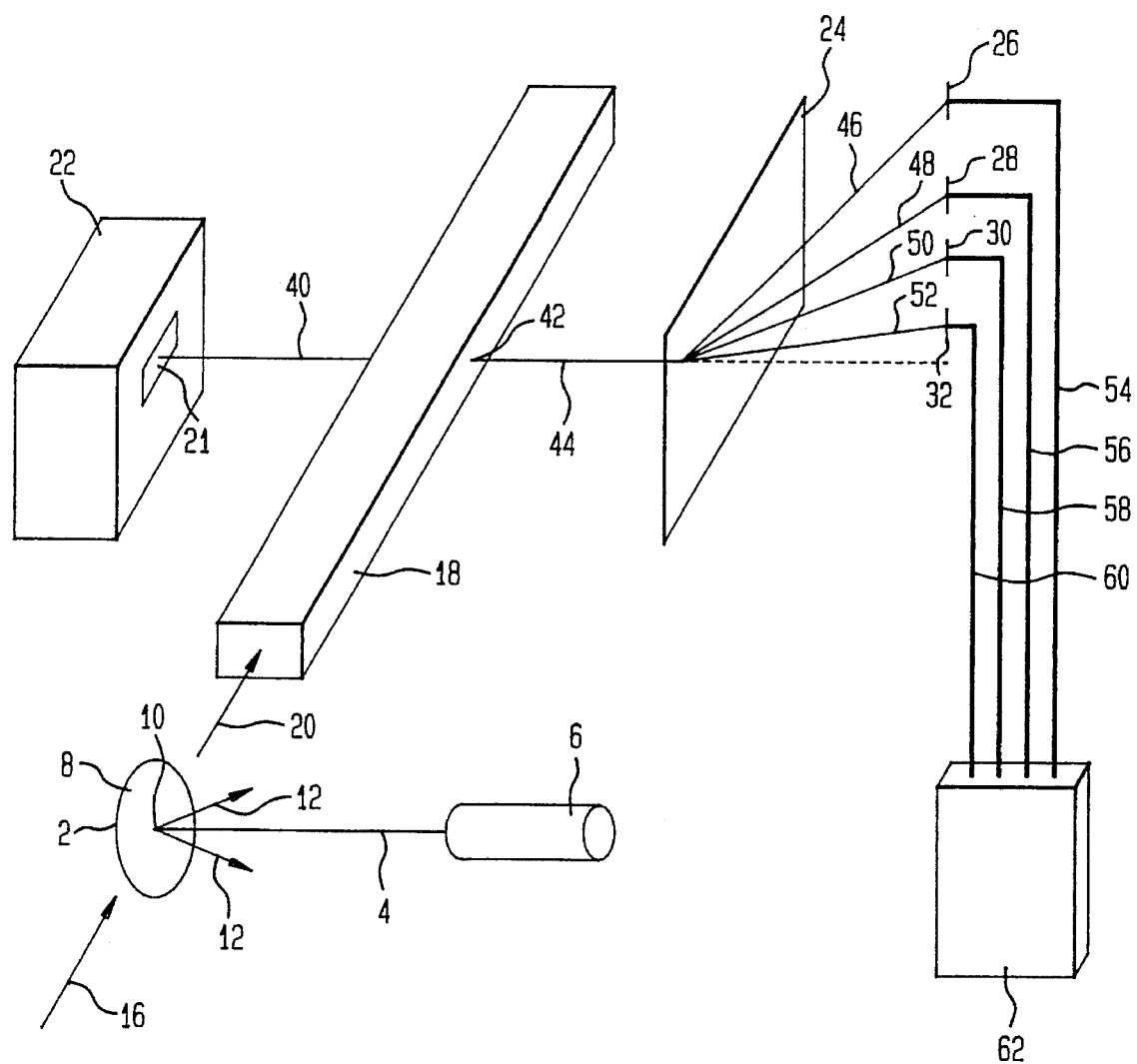
FIG. 1 is a schematic diagram of an embodiment of the apparatus according to the present invention.

FIG. 1 is a schematic diagram of an apparatus, according to the present invention, for determining profiles of chemical constituents of a semiconductor wafer 2. Wafer 2 is contained within a chamber not shown. Wafer 2 is subjected to an ion beam 4 generated by ion beam source 6. The ion beam can be any ion beam, for example, an argon ion beam. The beam 4 etches material from the surface 8 of wafer 2 at location 10, generating in the immediate vicinity of location 10 particles represented by arrows 12. An inert gas stream 16, such as an argon gas stream, carries the particles 12 into tube 18 as shown by arrow 20. Tube 20 is preferably a quartz or pyrex tube having square or rectangular cross section. Tube 18 is fed into an absorbance spectrometer, which is represented by light source 22, tube 18, grating 24 and detectors 26, 28, 30 and 32. An absorbance spectrometer useful to practice the present invention is Hewlett Packard Model 8452A Diode Array Spectrophotometer; it will be apparent to those of skill in the art how to modify such an absorbance spectrometer to practice the present invention. Light source 22 of the absorbance spectrometer has a slit through which radiation beam 40 emerges collimated and passes through tube 18 at location 42. The beam emerges as beam 44, which passes through grating 24, which splits beam 44 into beams 46, 48 50 and 52. Each of these has a different wavelength $\lambda$ of beam 44 incident on the grating 44. Beams 46, 48, 50 and 52 are incident to detectors 26, 28, 30 and 32 respectively. Four detectors are shown for example only; in a typical apparatus there are many more detectors. Detectors 26, 28, 30 and 32 are connected by lines 54, 56, 58 and 60, respectively, to computer 62. At period intervals of time, as different samples flow through tube 18, the relative concentrations can be determined to generate a profile of each $X_j$ as a function of time which can correspond to a depth into the semiconductor wafer 2. Alternatively, a group of apparatus of FIG. 1 can be arranged side by side and measurements can be made at different locations in the tube 18 to generate a profile of each $X_j$ over the spatial separation of the apparatus.

Figure 2:
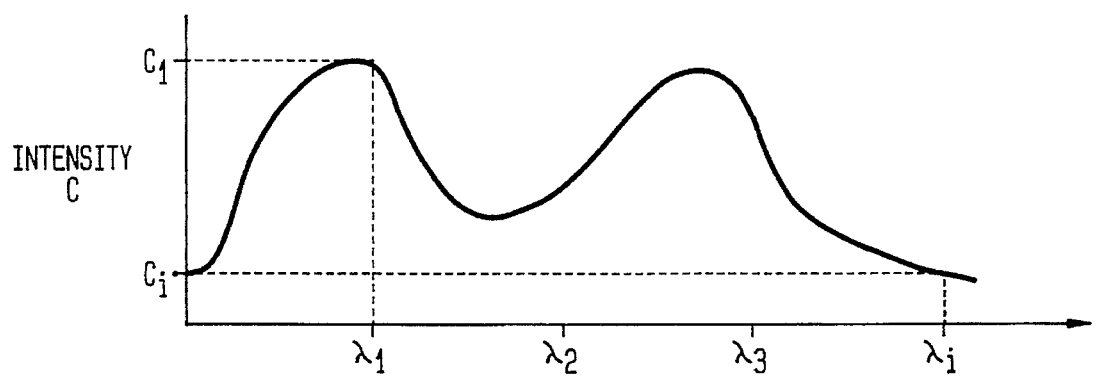
FIG. 2 is a schematic diagram of an absorption spectrum of a chemical combination.
Figure 3:
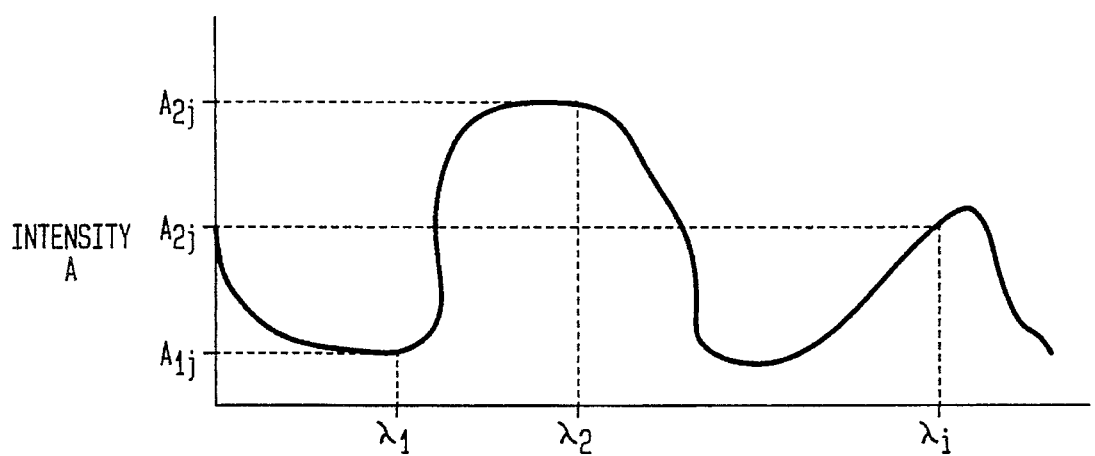
FIG. 3 is a schematic diagram of an absorption spectrum of the jth chemical constituent.

FIG. 2 is a schematic diagram of an absorption spectrum of a chemical combination, and FIG. 3 is a schematic diagram of the jth chemical constituent.

Before gas stream 20 is permitted to flow into tube 18, beam 40 is allowed to irradiate tube 18 so that computer 62 can record an intensity at each of the detectors. This is done because for each wavelength $\lambda$ the detectors will have a different sensitivity, represented by $I_0(\lambda)$. Gas stream 20 is then permitted to flow through tube 18; next, incident beam 40 from light source 22 passes through tube 18, which contains the gas stream 20. Detectors 26, 28, 30 and 32 now measure the radiation intensity, after passing through gas stream 20, as $I(\lambda)$. If there is no absorption at a particular wavelength, the ratio of I to I0 is 1. The absorption spectrum can be represented by the plot of either this ratio or its reciprocal. (The amount absorbed is proportional to 1 minus the former ratio.) The values of the most convenient ratio $R(\lambda)$ are stored in computer 20 for all values of $\lambda$.

Since it is known what are the expected chemical constituents of the gas stream 20, the absorption spectrum of each constituent is also measured and stored in computer 20. The absorption spectrum of each constituent can be measured using the Hewlett Packard Model 8452A Diode Array Spectrophotometer by inserting into the spectrophotometer a quartz or pyrex Cuvett filled with the particular chemical constituent.

A spectrum is generated as described above for each chemical constituent. Each of the j=1 to N chemical constituents is measured, and the absorbance values $A_{ij}$ at wavelengths $\lambda_i$, where i=1 to M, are stored in computer 20. The absorption spectrum of the composite sample, which is comprised of at least one of the chemical constituents, is measured, and the value of the absorbance $C_i$ at $\lambda_i$ of the composite sample is stored in computer 20. The absorbance $C_i$ is equal to a linear combination of the absorbances of all the chemical constituents, wherein each chemical constituent has a quantity or a concentration $X_j$, and is represented by the following equation:

$$C_i = \sum_{j=1}^{N} A_{i,j} X_j \tag{1}$$

For the composite sample, the value $X_j$ either can be the mass of the jth constituent, or can be the fractional amount of the total sample mass when this total has known value. Equation 1 can be represented in matrix form as equation 2:

$$C = AX \tag{2}$$

wherein C is a column vector having elements ($C_1, C_2, C_3, \ldots C_M$), wherein X is the column vector having elements ($X_1, X_2, X_3, \ldots X_N$), and wherein matrix A is a matrix of the elements $A_{ij}$. If matrix A has an inverse $A^{-1}$, the Equation 2 has a solution.

$$X = A^{-1} C \tag{3}$$

But A has an inverse only if the matrix A is square and are linearly independent. However, in this case the resulting values of the concentrations $X_j$ will then have rather sensitive dependence on the values of the matrix elements $A_{ij}$, so that slight measurement errors in matrix elements $A_{ij}$ may generate appreciable errors in computed amounts $X_j$.

To reduce such $X_j$ errors, it is desirable to incorporate measured values of both sample spectrum and component spectra at more wavelengths, that is, to make and use measurements at more wavelengths than there are constituent chemical components. Then M>N. Indeed, choosing M significantly larger than N admits a substantially greater amount of data sampling, which will yield a more precise determination of the concentrations $X_j$ of the chemical constituents.

But, in Equation 2, A is now no longer a square matrix. Therefore, another procedure is needed to determine the values $X_j$.

Filed on the same day, and incorporated here by reference, has been Kurtzberg et al., U.S. application Ser. No. 08/325, 746, entitled "Error Minimization Apparatus and Method for Real-Time Spectral Deconvolution of Chemical Mixtures". This incorporated application gives a procedure that usually treats this situation. It is possible that this procedure can yield non-unique equivalent decompositions, whenever, at all wavelengths $\lambda_1$ chosen for spectral measurements, two different non-negative linear combinations of such spectral values $(A_{1j}, A_{2j}, \ldots A_{Mj})$, for j=1 to N, can produce identical synthesized spectra. Then the requirements $0 \leq X_j$, wherein j=1 to N, restrict the possible vectors $X_1, X_2, \ldots, X_N$ to only a line segment, or a convex polygon, or some higher-dimensional polyhedron in N dimensional space. Inherently, the data cannot then furnish unique decomposition into chemical constituents, but here an alternative method can yield a most probable decomposition. This section first reviews the prior method, then expounds the new method. Throughout this discussion, the word "relative" embraces both absolute and relative $X_j$.

In order that one may more easily understand the concept of the prior procedure, this exposition describes that procedure in a simple but representative case that uses measurements at quite few wavelengths $\lambda_i$. This case assumes that one has also the total mass Z of the chemical mixture of interest. However, the procedure yields the desired values $X_j$ even when one lacks this total mass and when one uses many wavelengths.

In this special case, each mass $X_j$ must be not less than zero, and the sum of all $X_j$ must equal Z. (For example, if Z is 10 grams, then the $X_j$ will be non-negative masses whose sum is 10 grams.) Thus each $X_j$ must be not greater than Z, and if a particular $X_j$ equals Z then the chemical mixture contains only the jth constituent. If Z is a known mass, then one can use Z for convenience to normalize the values $X_j$; that is, one can seek the quotients $X_j/Z$ and call these $X_1, X_2, \ldots, X_N$. Then the following relations define a region of allowable values for these normalized $X_j$:

$$0 \leq X_j \leq 1 \tag{4}$$

$$\sum_{j=1}^{N} X_j = 1 \tag{5}$$

Figure 4:
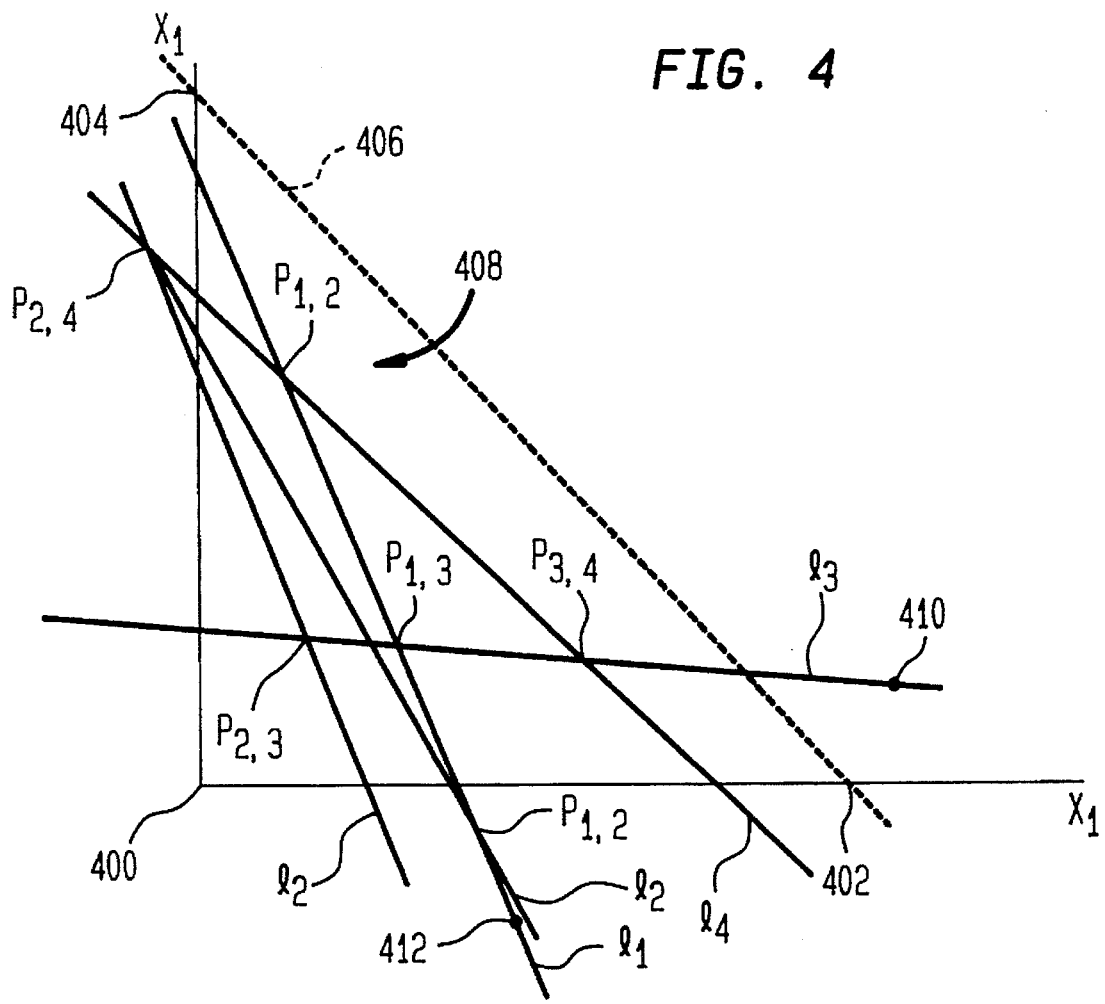
FIG. 4 shows, in a two dimensional domain of relative concentrations, intersections defining possible solutions for relative concentrations within an allowed domain for a description of a chemical combination containing two constituents.

FIG. 4 shows an example in only two dimensions—the simplest interesting situation. There the sample mixture has just two constituents—in normalized relative amounts $X_1$ and $X_2$. By Equation 6, $X_1$ has range between 0 and 1, i.e., between points 400 and 402 in FIG. 4. Likewise, $X_2$ has range between 0 and 1, i.e., between points 400 and 404. In such two-dimensional cases, Equation 5 becomes simply Equation 6.

$$X_1 + X_2 = 1 \tag{6}$$

In FIG. 4, Equation 6 determines straight line 406 between points 402 and 404. Thus the allowed values of pairs $(X_1, X_2)$ must be points of the triangular region 408— the region whose bounds are the line 406 together with the $X_1$ and $X_2$ coordinate axes. Points outside this region, like points 410 and 412 in FIG. 4, have coordinates that are not allowed values.

In this case, where the the chemical mixture has only two possible constituents, equation 1 reduces to Equation 7, which in FIG. 4 determines a straight line for each possible i wherein i=1 to M.

$$C_i = A_{i,1} X_1 + A_{i,2} X_2 \qquad (7)$$

The subscript i, as described herein above, corresponds to a wavelength $\lambda_i$ at which the apparatus measures spectrum values. If the apparatus uses four such wavelengths $\lambda_i$, then Equation 7 determines four straight lines: $l_1, l_2, l_3,$ and $l_4$, as shown in FIG. 4. If coefficient pair $(A_{1,1}, A_{1,2})$ for line $l_1$ and corresponding pair $(A_{2,1}, A_{2,2})$ for line $l_2$ are linearly independent, that is, if $l_1$ is not parallel to $l_2$, then line $l_1$ will intersect line $l_2$ at some point which in FIG. 4 is shown as point $p_{1,2}$. Lines $l_3$ and $l_4$ are shown intersecting in point $P_{3,4}$. Lines $l_2$ and $l_3$ are shown intersecting at point $P_{2,4}$. Lines $l_2$ and $l_4$ are shown intersecting at point $P_{2,4}$. Line $l_1$ intersects line $l_2$ at point $P_{1,2}$. Line $l_1$ intersects line $l_3$ at point $P_{1,3}$. Since points $P_{2,4}$ and points $P_{1,2}$ are outside the allowed region 408, they do not represent points having allowed coordinates. This leaves points $P_{1,2}$, $P_{3,4}$, $P_{1,3}$, and $P_{2,3}$ as points of intersection within the allowed region 408.

For the lines with Equations 7, finding intersections of pairs poses merely several problems like Equation 2, where A is a square matrix; hence A has an inverse, and Equation 3 gives the solution. Thus taking lines $l_i$ two at a time and using Equation 3 on each pair yields values $X_1$ and $X_2$ which satisfy the equations for both lines $l_1$ and $l_2$. However, for the lines with Equations 7, if the intersection point of any pair is a point of the allowed region satisfying Equations 4 and 5, then this point is a candidate for best approximation to a solution of the whole Equation-set 7 for i=1 to 4. Still, from among all such intersections, some procedure must determine which provides the best set of $X_j$ values. Such a procedure needs a measure of the error. Here Equation 8 defines the error $\epsilon$ to be the sum of the absolute values of the errors $\epsilon_i$ in Equations 7 for i=1 to M. That is, $$\epsilon = \sum_{i=1}^{M} |\epsilon_i| \qquad (8)$$

The errors $\epsilon_i$ of equation 8 correspond to a particular intersection point. To indicate this more clearly, rewrite Equation 8 as Equation 9:

$$\epsilon(\{X_j'\}) = \sum_{i=1}^{N} |\epsilon_i(\{X_j'\})| \qquad (9)$$

That is $\{X'_j\}$ indicates the coordinates of a particular point in one of the intersections, for example point $P_{1,2}$ of FIG. 4. The value of $\epsilon_i$ is given by Equation 10.

$$\epsilon_i(\{X_j'\}) = \sum_{j=1}^{N} A_{ij} X_j' - C_i \qquad (10)$$

For the simple case shown in FIG. 4, Equation 8 reduces to Equation 11.

$$\epsilon = |\epsilon_1| + |\epsilon_2| + |\epsilon_3| + |\epsilon_4| \qquad (11)$$

Thus Equation 11 takes the following form, wherein point $P_{1,2}$ of FIG. 4 represents the coordinates $(X_1, X_2)$.

$$\epsilon(P_{1,2}) = |\epsilon_1(P_{1,2})| + |\epsilon_2(P_{1,2})| + |\epsilon_3(P_{1,2})| + |\epsilon_4(P_{1,2})| \qquad (12)$$

But $\epsilon_1(P_{1,2})$ and $\epsilon_2(P_{1,2})$ are both zero, since the intersection $P_{1,2}$ is on both lines $l_1$ and $l_2$; whereas $\epsilon_3(P_{1,2})$ and $\epsilon_4(P_{1,2})$ are both non-zero, since generally the intersection $P_{1,2}$ is not on lines $l_3$ and $l_4$. These non-zero errors, $\epsilon_3$ and $\epsilon_4$, represent essentially the facts that the intersection $P_{1,2}$ is on neither line 3 nor line 4, respectively. The simplest situation is shown in the two-dimensional example of FIG. 4. If the spectra are obtained at a large number of wavelengths, then the number of intersections increases significantly. From Equation 7, each wavelength generates a line; so, for example, if the number of wavelengths is 100, then there are 100 lines that can intersect. However, lines intersect in pairs, whence there are 4950 possible points of intersection in the allowed region. In the general case, there can be a large number of wavelengths, and a large number of dimensions, that is, of constituents for which values of $X_j$ are being determined. It can be shown that some intersection point minimizes the error $\epsilon$, but there can be a very large number of intersections that are possible solutions for the $X_j$ values. Thus, it is desirable that a simple procedure should determine which one of these intersections produces the minimum error.

In the general case, Equation 1 defines a set of M surfaces (hyperplanes) of dimension N–1 in an N dimensional space. These M surfaces intersect within the N dimensional space to yield the intersection points. Those points that are in the allowed region defined by Equations 4 and 5 are possible solutions for the N values of $X_j$. Which one of these intersections provides the minimum error $\epsilon$, as defined by Equation 8, is determined by linear programming. Linear programming is a technique well known in the art. In the general case, Equation 1 defines a set of N–1 dimensional surfaces which intersect to define points in the N dimensional space, lines in the N dimensional space and surfaces in the N dimensional space.

The set satisfying all conditions is a polytope (generalized polyhedron) in this N dimensional space. Some vertex of this polytope is a point of minimum error. There can be more than one point which has this minimum error. Two points having the same minimum error will be connected by a line segment in the N dimensional space along which the points have the same minimum error. Indeed, there can be more than two points having the same minimum error; then these points will lie in a lower-dimensional polytope on the surface of the previously mentioned one, and all points in this lower-dimensional set will have the same minimal error.

Figure 6:
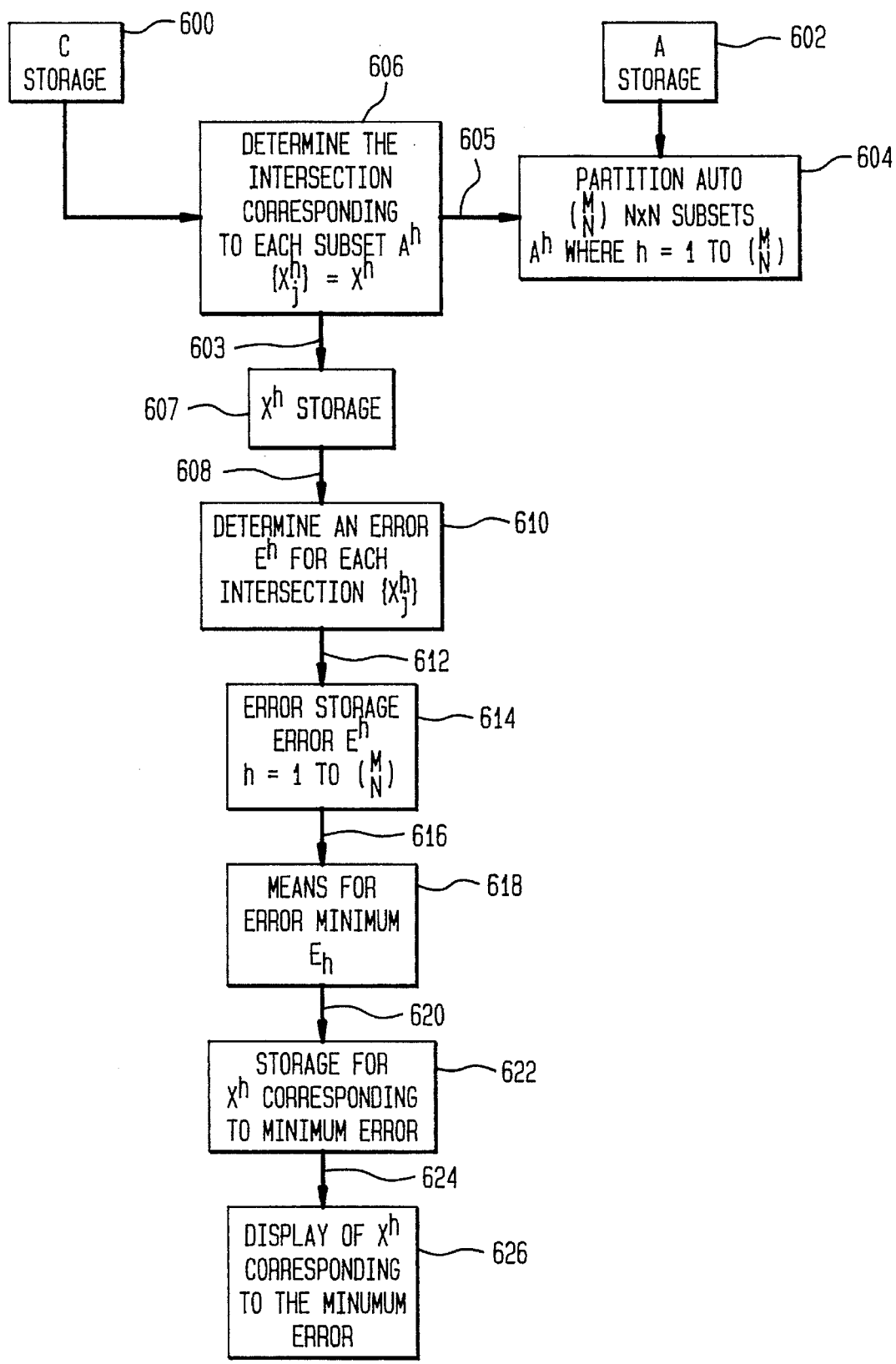
FIG. 6 is a flow chart of the method for determining the relative concentrations of chemical constituents having a minimum error.

Among other programs, the LSO package of IBM can be used to solve efficiently, via the simplex method, the incidental linear programming problems of this invention. FIG. 6 describes the computation, and labels the data storage locations. The previously measured coefficients $A_{ij}$ having been placed in A storage 602, the newly measured spectral intensities $C_i$ having been sent to C storage 600, LSO reads the data from these designated locations, computes the desired values of the $X_j$, and communicates them in any of several alternative ways.

Figure 5:
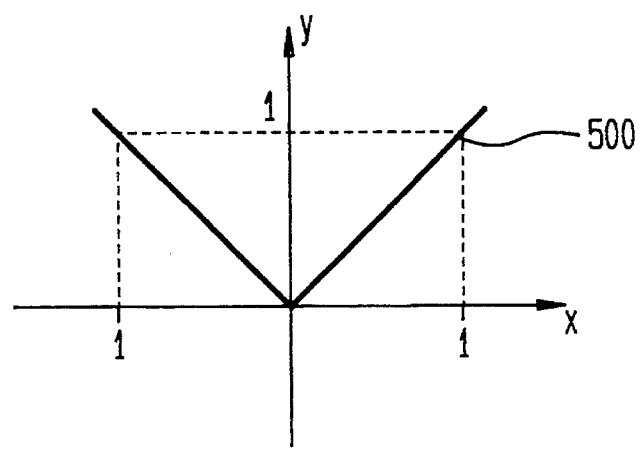
FIG. 5 shows a plot of an absolute value function.

An intersection with minimum error can be determined in more than one way. Equation 9 determines the error as the sum of the absolute value of the suberrors errors $\epsilon_i$. However, the absolute value is not a linear function. Indeed, for Equation 13, FIG. 5 displays the plot as a curve 500, which is clearly not a straight line.

$$y = |x| \qquad (13)$$

But linear programming works only with linear relations. Therefore Equation 8 cannot be used in the linear programming technique to determine the intersection having minimum error $\epsilon$. A technique is needed to introduce effectively the substance of Equation 8 by means of linear equations. This is done by replacing Equation 8 with Equation 14, wherein $u_i$ and $v_i$ are additional variables satisfying Equations 15 and 16, wherein i=1 to M.

$$\epsilon = \sum_{i=1}^{M} (u_i + v_i) \quad (14)$$

$$u_i - v_i = C_j - \sum_{j=1}^{N} A_{i,j} X_j \quad (15)$$

$$u_i \geq 0, v_i \geq 0 \quad (16)$$

Here the variables $u_i$, $v_i$, and $X_j$ can take any non-negative values, but the desired minimization forces either $u_i$ or $v_i$ to be zero for each i. Indeed, if some $u_i$ and $v_i$ satisfy Equations 15 and 16 for each i, but if neither value is zero, then for $u_i$ and $v_i$ we can substitute $$v'_i = v_i - min(u_i, v_i), u'_i = u_i - min(u_i, v_i) \quad (17)$$

The new values satisfy Equations 15 and 16, but decrease $\epsilon$; so, together, positive $u_i$ and $v_i$ cannot yield minimum $\epsilon$. Accordingly if, for i=1 to M, some values $u_i$ and $v_i$ yield minimum $\epsilon$, then for each pair, by Equation 14, one is zero, the other is $|\epsilon_i|$, and $$|\epsilon_i| = u_i + v_i \quad (18)$$

Hence this reformulation produces the same minimum $\epsilon$, though it involves only linear relations.

An alternative goal is to minimize a different error expression $\epsilon'$—that given by Equation 19, or equivalently, as is well known, by Equation 20.

$$\epsilon' = max(|\epsilon_1|, \ldots, |\epsilon_M|) \quad (19)$$

$$\epsilon' = \lim_{p \to \infty} p\sqrt{\sum_{i=1}^{M} \left( \sum_{j=1}^{N} A_{i,j} Xj - C_i \right)^p} \quad (20)$$

A slightly different trick reduces this also to a problem involving only linear relations, and thus to a problem solvable by linear programming. We add just one new variable u, defined to satisfy $$u \geq \epsilon_i, u \geq -\epsilon_i \quad (21)$$

wherein i=1 to M. This new u and the prior variables satisfy only linear relations, and we seek to minimize this u. Thus one can use linear programming to minimize $\epsilon'$ also.

FIG. 6 is an embodiment of a routine which runs on 62 of FIG. 1 to determine the best intersection point, i.e., the point giving the relative concentrations $X_j$ having minimum error $\epsilon$. The relative spectral intentions $C_i$ are stored in C storage 600. The relative constituent spectral intensities $A_{ij}$ are stored in the A storage 602. As indicated by block 604, to get an N-by-N submatrix we can choose N rows in C(M,N) ways from the M-by-N matrix $(A_{ij})$ in storage A, where C(M,N)=M!/(N!(M−N)!). These submatrices we label $A^h$, where h=1 to C(M,N).

One of the submatrices $A^h$ is transferred to block 606, as indicated by line 605. At block 606 an intersection corresponding to the submatrix $A^h$ has a set of solutions $X_j$ represented by left bracket $\{X_j^j\}$, which is determined from an equation such as Equation 3. In matrix notation there is a vector $X^h$ which contains the values of the relative concentrations determined from the $A^h$ subset. As indicated by lines 608, the values of the relative concentrations $\{X^h\}$ are passed to block 610, where an error $\epsilon^h$ is determined therefor. As indicated by lines 612, this error is passed to error storage 614 which can store the most recent of the errors for h=1 to C(M,N).

A straightforward but inefficient procedure might then pass these errors, as indicated by line 616, to a means 618 for choosing the minimum of the error values $\epsilon^h$. As indicated by line 620, the values of the relative spectral intensities $X^h$ corresponding to the minimum error are passed to storage 622. The values of the relative spectral intensities $X^h$ corresponding to the minimum error can be sent, as indicated by line 624, to a display device indicated by block 626. The display device can be a printout, or can be a visual display on a terminal, such as a plot, or the like.

However, the preferred embodiment of the minimization, namely, the simplex method of linear programming, greatly shortens the search, since usually it obtains the intersection point of minimum error $\epsilon$ while determining only a small subset of all $X^h$ and the corresponding errors. That is, a starting procedure obtains one intersection point $X^h$, and then the method traverses some other intersection points and reaches the minimum-error point without calculating all the others. When the simplex method, in its progress, reaches any intersection point $X^h$, an appropriate storage unit contains a tableau of relevant numerical values. Then a so-called "pivot step" replaces this tableau by the corresponding tableau for an adjacent intersection having smaller error. Succeeding pivot steps further reduce the error until the tableau indicates that no possible step can achieve less error.

Among other programs, the LSO package of IBM can be used to solve efficiently, via the simplex method, the incidental linear programming problems of this invention. FIG. 6 describes the computation, and labels the data storage locations. The previously measured coefficients $A_{ij}$ having been placed in A storage 602, the newly measured spectral intensities $C_i$ having been sent to C storage 600, LSO reads the data from these designated locations, computes the desired values of the $X_j$, and communicates them in any of several alternative ways.

This discussion now treats the examples that motivate the new method. FIG. 1 shows material 20 passing through tube 18 at periodic intervals—to undergo measurements then stored in computer 22. However, more generally one can consider also a "space sample"—a mechanism that captures and analyzes simultaneous (or nearly simultaneous) spectral data from a finite plurality of locations in subject chemical mixture. Alternatively, the matrix $(A_{ij})$ may lack full rank, so that spectral measurements of the mixture at a single location and time may yield a continuum of possible decompositions into chemical constituents. In the latter case, one can discretize the set of possible decompositions, i.e., partition this set into a finite number of convenient distinct subsets and choose a representative point from each subset. Thus again, for a single instant of time one can get a "space sample"—a finite plurality of analyses that offer possible decompositions at that instant. In the following, a "time sample" will mean a sequence of space samples at a finite plurality of times—in general, at periodic intervals.

Thus the source for a space sample can be a finite plurality of separate radiation sources 22 as in FIG. 1, collectively emitting a plurality of beams 40 directed at tube 18, and traversing a plurality of detection and measurement apparatus, including diffraction gratings 24 and detectors such as 26 to 32. Otherwise, at a finite plurality of locations within a chemical mixture, local radiation sources may provide spectra for detection and measurement as in FIG. 1. Alternatively, a finite plurality of separate radiation sources may provide spectra for detection and measurement by a plurality of apparatuses, each as in FIG. 1, and each recording its measured data in computer 62. In any event, each space sample offers at least one computed decomposition $X = (X_1, X_2, \ldots, X_N)$ of the subject mixture into absolute or relative quantities of chemical constituents.

Figure 7:
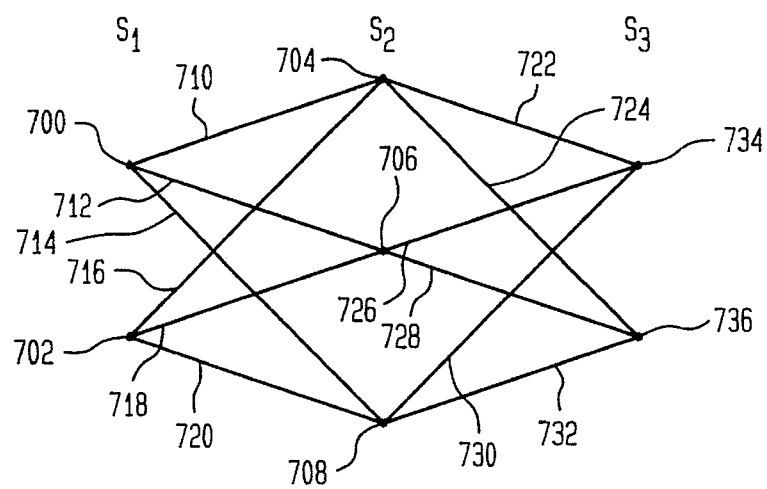
FIG. 7 is a schematic diagram of an arrangement of sets of relative concentrations having substantially the same minimum error for three samples and transitions between the sets of relative concentrations for each sample.

FIG. 7 shows schematically the results of measuring three space samples S, $S_2$, and $S_3$, which can be samples all at one time or at three consecutive times. Sample $S_1$ has two decompositions X, represented by points 700 and 702. Sample $S_2$ has three decompositions, points 704, 705, and 708. Sample $S_3$ has two decompositions, points 734 and 736. In an actual profiling experiment one would have a relatively large number of samples, but FIG. 7 shows only three samples in order to represent simply how the present invention selects the most likely profile from amongst the many possible choices.

If the method of the prior review has analyzed one radiation source into multiple decompositions, then necessarily each decomposition has the same error—in the sense of the prior remarks. Indeed, one can generalize the present technique by admitting decompositions that have just slightly greater error. If separate beams or sources have yielded multiple decompositions, then these decompositions still have substantially the same errors. Thus points 700 and 702 in sample $S_1$ have substantially the same error, as do points 704, 706, and 708 in sample $S_2$, and as do points 734 and 736 in sample $S_3$.

In FIG. 7, the line segments between points represent transitions from the (tentative) decompositions of one sample to those of the next sample. Thus usually samples connected by lines represent measurements at consecutive times. Here, point 700 of $S_1$ can have transitions to points 704, 706, and 708 of $S_2$, these transitions shown respectively as lines 710, 712, and 714. Also, point 702 of $S_2$ can have transitions to points 704, 706, and 708 of $S_3$, these transitions shown respectively as lines 716, 718, and 720. Likewise, point 704 of sample $S_2$ can have transitions to points 734 and 736 of $S_3$, these transitions shown respectively as lines 722 and 724. Likewise, point 706 of sample $S_2$ can have transitions to points 734 and 736 of $S_3$, these transitions shown respectively as lines 726 and 728. Likewise, point 708 of sample $S_2$ can have transitions to points 734 and 736 of $S_3$, these transitions shown respectively as lines 730 and 732.

FIG. 7 admits 12 possible paths in temporal order—through the points that represent decompositions, by way of the lines that represent transitions. An invention here is a system, method, and apparatus for choosing the most likely path, that is, the one having the largest probability, from amongst the many possible paths through the points and line segments forming the network of FIG. 7. Here, as usual, probabilities are numbers between 0 and 1, while the probability of two independent events is the product of their separate probabilities. By inspection one finds the most likely path to each point of $S_1$. From this information one finds the most likely path to each point of $S_2$. From this information one finds the most likely path to each point of $S_3$, via a stage-by-stage procedure.

Prior experiments and tabulated chemical results can furnish transition probabilities to enter these computations; and computer 62 of FIG. 1 can provide a lookup table in which to store required quantities. Alternatively, computational means, applying basic physical and chemical principles, can evaluate transition probabilities. Together, these means supply the needed values.

Here, the points 700 and 702 of $S_1$ are given starting points, so one reaches either with probability 1. However, any path to a chosen point 704, 706, and 708—the points of $S_2$—has two sections: a path to one of the preceding points 700 and 702—the points of $S_1$—and then a transition to the chosen $S_2$ point. Moreover, the probability of following any such path is just the probability (here, unity) of following that path to its $S_1$ point, times the transition probability from this $S_1$ point to the chosen $S_2$ point: 704, 706, or 708. Thereby one can compute the probability of the one (hence, best) path through every $S_1$ point to every $S_2$ point; so, for each $S_2$ point, one can make a decision which path to that point has the largest probability, and one can exclude from consideration any other path to that point.

Likewise, any path to a chosen point 734 or 736—the points of $S_3$—has two sections: a path to one of the preceding points 704, 706, and 708—the points of $S_2$—and then a transition to the chosen $S_3$ point. Moreover, the probability of following any such path is just the probability of following that path to its $S_2$ point, times the transition probability from this $S_2$ point to the chosen $S_3$ point: 734 or 736. To this point one seeks the most probable path, but one has already determined the most probable path to each $S_2$ point, and has excluded from consideration all other paths to that $S_2$. Thus one can compute the probability of the best path through every $S_2$ point to every $S_3$ point; so, for each $S_3$ point, one can make a decision which path to that point has the largest probability.

If the network of FIG. 7 included a later-time space sample $S_4$, then one would iterate the sketched procedure, excluding all but the most probable path to each $S_3$ point. Moreover, during this procedure one can delete successively those line segments playing no part in the most likely paths to points first in $S_1$, then in $S_2$ and so forth. The outcome of all such deletions is the most likely path with the given transition probabilities. Indeed, two points of such a network may represent such incompatible decompositions $(X_1, X_2, \ldots, X_N)$ that between these decompositions the transition probability is manifestly zero, the corresponding transition is non-allowed, and the corresponding line segment may be excluded a priori.

Figure 8:
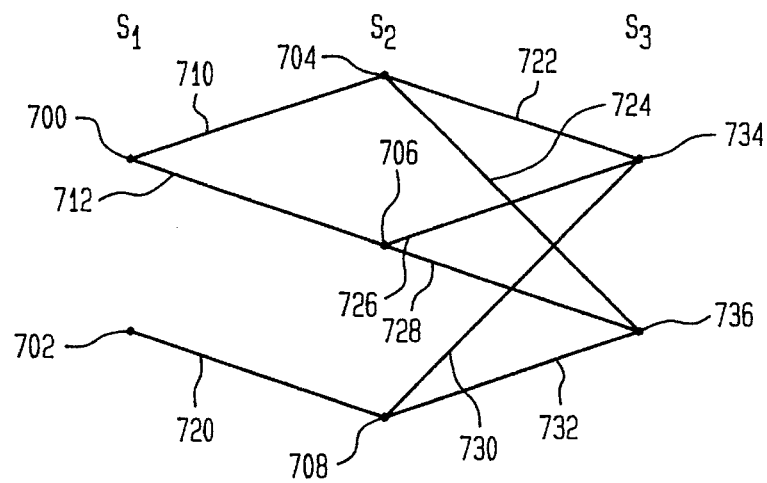
FIG. 8 is a schematic diagram corresponding to the diagram of FIG. 7 wherein some of the transitions between sets of relative concentrations between sample 1 and sample 2 are eliminated as having a lower probability than other transitions.

FIG. 8 shows the same point array as FIG. 7, but, by the method of this discussion, it eliminates some transitions between samples $S_1$ and $S_2$. One can drop neither point 700 nor point 702, since each has probability 1; and the corresponding decompositions have roughly equal errors, so that one cannot prefer either on error-size considerations. However, FIG. 8 supposes that transition 720 outperforms transition 714 to point 708, that transition 710 outperforms transition 716 to point 704, and that transition 712 outperforms transition 718 to point 708.

Figure 9:
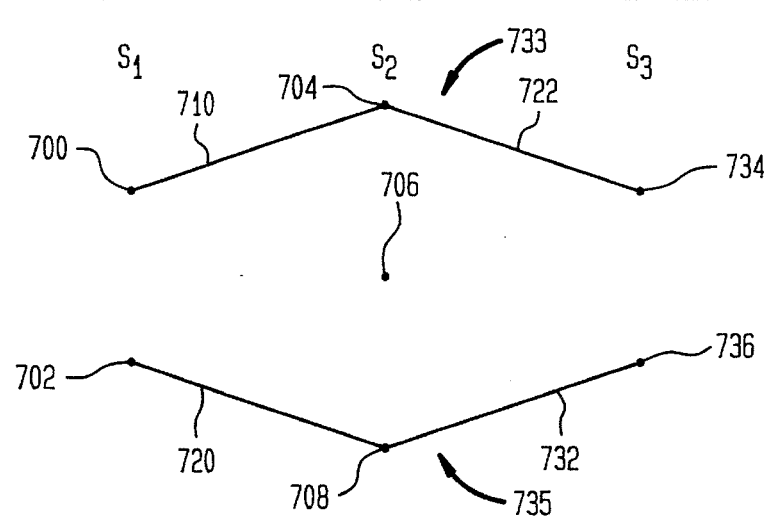
FIG. 9 is a schematic diagram similar to that of FIG. 8 wherein transitions are eliminated between sets of relative concentrations between sample 2 and sample 3 as having lower probability than other transitions.

FIG. 9 shows the same point array as FIG. 8, where now, by the method of this discussion, it eliminates also some transitions between samples $S_2$ and $S_3$. Indeed, FIG. 9 supposes that transition 722 outperforms transitions 726 and 730 to point 734, and that transition 732 outperforms transitions 724 and 728 to point 736. The Figure expresses the fact that, for the most likely path to point 734, the probability is the product of the probabilities for point 700, transition 710, and transition 722, whereas, for the most likely path to point 736, the probability is the product of the probabilities for point 702, transition 7 20, and transition 732.

If $S_3$ is the last sample, then one compares the two final most likely paths—those to points 734 and 736—and one chooses the path with greater probability. However, the points on this path represent decompositions $(X_1, X_2, \ldots, X_N)$ of the chemical mixture, and these decompositions then constitute the most likely profile. Clearly, in this simple illustrative case, one might compute probabilities for all paths. However, if a time sample presents many space samples, and each space sample comprises many possible decompositions, then the analogue of FIG. 7 is a network with quite many points and line segments. But then finding probabilities for all paths is a severe test of even a very fast computer—and is an unnecessary test, since the preceding example indicates that this method, essentially dynamic programming, effects the desired optimization with far less computational effort.

Dynamic programming references include the following:
G. B. Dantzig, On the shortest route path through a network, Management Science, v. 6, 1960, pp. 187–190.
A. Kaufmann and R. Faure, Introduction to Operations Research, Academic Press, New York 1968, Chapter 2.
Barry Render and Ralph M. Stair, Jr., Quantitative Analysis for Management, Allyn and Bacon, New York 1994, Module C.

Dynamic programming has discrete and continuous forms, but the present invention needs just the discrete form, so those remarks treat only discrete problems. Such problems may take various guises, but with any such, one can associate a finite network, similar to FIG. 7, in which every line segment has a specified allowable direction. This network has a designated initial node, and has a designated final node. (Given several initial nodes one can add an auxiliary node preceding them all; given several final nodes one can add an auxiliary node following them all.) If a path with r segments, but no path with fewer segments, connects the initial node with a given node N, then one assigns this node N to the "rth stage". With every segment one associates a real number; with every path one associates the sum of the numbers for the component segments. (In the preceding example, one does not add segment values. Rather, one multiplies transition probabilities, but equivalently one might add logarithms of probabilities.) One seeks a path that connects initial node with final node, and that has maximum (or minimum) associated sum.

Essentially, one solves this general problem much as one solves the preceding example: for r=0, then r=1, then r=2, and so forth, one solves the corresponding problem for each rth-stage node. The 0th-stage problem has a trivial solution, since it involves only the initial node. However, the optimal path to any (r+1)th-stage node N must follow an r-step path to some rth-stage node M, then add just one segment MN—from M to N. But one can easily choose the optimum among all rth-stage nodes M just one segment before N: the preceding stage of the calculation has previously found the optimal path and corresponding sum for each possible M, and the statement of the problem associates a given quantity with the remaining segment MN. For the optimal path to each N, one need store only the associated sum and the preceding node M.

After the rth stage of the calculation, for r=0, 1, 2, . . . , one can delete any segment that enters no rth-stage partial solution. These deletions display graphically that dynamic programming obviates computing many non-optimal path-sums. Indeed, it leaves only the optimal path when that path reaches the final node. From the stored results, one extracts the optimal path by tracing it backward from the final node, an unambiguous task, since the prior deletions have left each relevant node just one predecessor.

Figure 10:
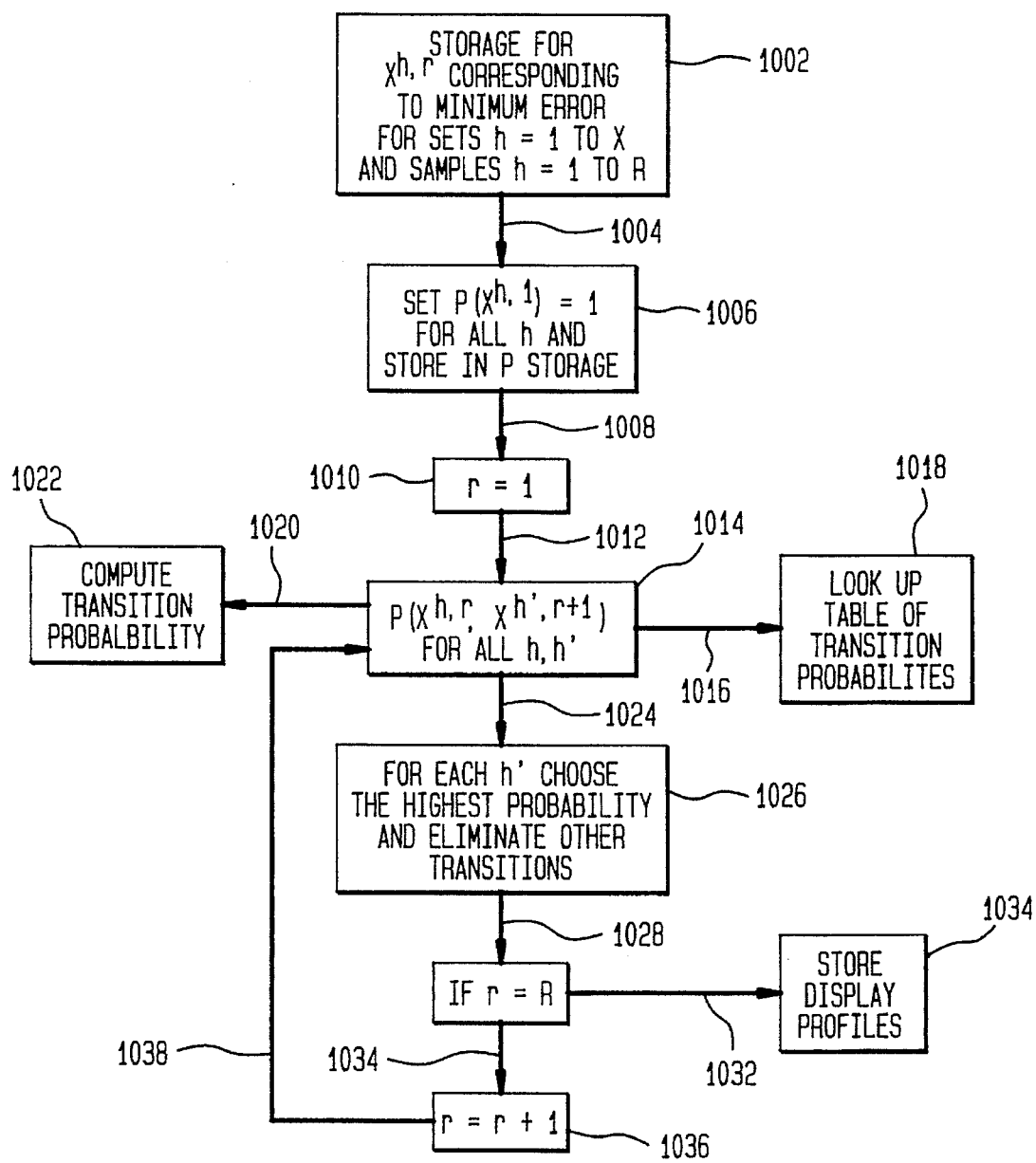
FIG. 10 is a schematic diagram of a system according to the present invention for determining profiles having highest probability over sets of relative concentrations for a plurality of samples.

FIG. 10 schematically diagrams a routine that accepts a network, like that of FIG. 7, and selects the path of greatest probability between its initial and final nodes. More generally, as in FIG. 7, one supposes finite sets $S_1, S_2, \ldots, S_H$ of decomposition vectors $(X_1, X_2, \ldots, X_N)$ where the measurement protocol determines the positive integer H. Moreover, one supposes X-vectors $X^{h,1}, X^{h,2}, \ldots, X^{h,K}$ in $S_h$, where each h determines a different integer K(h). In general, the $S_h$ are the required computational stages; in FIG. 7 and this invention, they are space-samples. One obtains these X-vectors either from nearly simultaneous measurements of the chemical mixture, or from non-unique outcomes of the linear-programming method, or from that method's proposed extension to not-quite-minimal errors. Hence, within each set $S_h$, all vectors $X^{h,k}$ have substantially the same error. In FIG. 7, for example points 700 and 702 of sample $S_1$ have roughly equal error.

In FIG. 10, box 1002 provides storage for the vectors $X^{h,k}$. Line 1004 indicates that the program then transfers the $X^{h,k}$ data from box 1002 to box 1006, where, for all initial vectors (i.e., all vectors $X^{l,k}$) it sets the probabilities equal to 1, and puts these values in other storage locations. Line 1008 shows that the routine next transfers program control to box 1010, where it initializes integer r to value 1. Line 1012 indicates that the routine then transfers program control to box 1014, wherein it determines the needed X-vector transition probabilities: either it transfers control by 1016 to box 1018, which contains lookup tables, or it transfers control by 1020 to box 1022, which computes the desired values.

If the linear-programming method yields, among other decompositions, vectors $X^{h,k}$ and $X^{q,s}$ in respectively $S_h$ and $S_q$, then each vector has minimum error, and again one may decide to accept not-quite-minimum error. Here, with this slight generalization of the admissible vectors, represents the transition probability from former to latter. However, the program needs only transition probabilities $P(X^{h,k}, X^{h+1,s})$, since the transitions connect only consecutive stage s or space-samples. The program determines these probabilities; in particular it determines those for which h=1, and multiplies them by the initial probabilities to get the probabilities of all paths to nodes of sample $S_2$. For each $S_2$ node, the program then chooses the path of greatest probability, and it eliminates all other such paths. In FIG. 7, for example, $S_1$ contains points 700 and 702, while $S_2$ contains points 704, 706, and 708. FIG. 8 shows FIG. 7 after such elimination has removed line segments 714, 716, and 718.

Now line 1028 indicates that the program transfers control to box 1030, which determines whether r has reached the value H, the number of the last space-sample or stage. If so, then line 1032 shows that the program transfers control to box 1034, which displays or stores profiles. If not then line 1035 shows that the program transfers control to box 1036, which replaces r by r+1. then line 1038 shows that the program returns control to box 1014, which repeats the loop, selecting most probable paths to nodes of the next space-sample or stage.

While the present invention has been shown and described with respect to specific embodiments, it should be understood that it is not thus limited. Numerous modifications, changes, and improvements will occur which fall within the scope and spirit of the invention.

We claim:

1. An apparatus having a computer for determining the most probable profile of concentrations of component chemical mixtures in a chemical mixture over a plurality of ordered samples of said chemical mixture, wherein there is a plurality of sets of relative concentrations for each of said samples comprising:

a first storage location in said computer for storing said plurality of sets of relative concentrations;

means for assigning a probability, and for storing said probability in a second storage location in said computer, to each of said sets of relative concentrations for an initial sample of said samples;

means for assigning a transition probability, and for storing said transition probability in a third storage location in said computer, for a transition from each of said sets of one of said ordered samples to each of said sets of the next ordered sample;

a processor in said computer for accumulating said transition probabilities in said third storage location assigned to each of said sets including said transition probabilities of all transitions from a set in said initial sample in said second storage location; and a processor on said computer for choosing, for each of said sets having more than one of said transitions, a transition resulting in the highest probability for said set and discarding all other transitions.

2. An apparatus according to claim 1 further including a means for determining concentrations, $X_j$ of N component chemical constituents wherein j=1 to N for each sample of said chemical mixture.

3. An apparatus according to claim 1, further including means for measuring relative spectral intensities $C_{i,k}$ for the kth ordered sample of said chemical combination at wavelength $\lambda_i$ for i=1 to M.

4. An apparatus according to claim 3, further including means for storing relative spectral intensities $A_{ij}$ of said N component chemical constituents.

5. An apparatus according to claim 4 wherein said $X_j$ for each of said samples is determined from said relative spectral intensities $C_{i,k}$ and said relative spectral intensities $A_{ij}$.

6. An apparatus according to claim 5, wherein said relative spectral intensities $A_{ij}$ and $C_{ij}$ are absorbance intensities.

7. An apparatus according to claim 5, further including said means for providing said relative spectral intensities $C_{i,k}$ is an absorbance spectrometer.

8. An apparatus according to claim 5, wherein said relative spectral intensities $A_{ij}$ are determined using an absorbance spectrometer.

9. An apparatus according to claim 2, wherein said means for determining is a digital computer.

10. An apparatus according to claim 9, wherein said predetermined relative spectral intensities $A_{ij}$ are stored in said digital computer.

11. An apparatus according to claim 5, wherein if a particular $X_j$ is determined to be less than zero, said particular $X_j$ is set equal to zero.

12. An apparatus according to claim 5, further including a means for generating said relative spectral intensities $C_{i,k}$ at a plurality of periodic intervals in time.

13. An apparatus according to claim 12, wherein said interval of time is less than a millisecond.

14. An apparatus according to claim 5, wherein said chemical mixture is selected from the group consisting of a solid, a liquid and a gas.

15. An apparatus according to claim 12, wherein said chemical mixture is a solid, and further including a means for removing a portion of material at a surface of said solid, said ordered samples of said chemical mixture being said portions at each of said plurality of said periodic time intervals each of said plurality of said periodic time intervals corresponding to a depth into said surface.

16. An apparatus for determining the most probable profile for concentrations $X_{j,k,l}$ of N component chemical constituents, wherein j=1 to N, in a chemical mixture over a plurality of K ordered samples, wherein k=1 to K, wherein there are L sets of concentrations for each of said samples, wherein l=1 to L and L≧1 for each of said samples using predetermined relative spectral intensities $A_{ij}$ of said N component chemical constituents at wavelength $\lambda_i$ comprising:

means for providing relative spectral intensities $C_{i,k,l}$ of said chemical mixture at wavelengths $\lambda_i$;

means for determining said concentrations $X_{j,k,l}$ from said relative spectral intensities $C_{i,k,l}$ and said predetermined relative spectral intensities $A_{ij}$;

an electromagnetic radiation source for providing an incident beam containing said $\lambda_i$, said incident beam having an intensity $I_0(\lambda_i)$ at each of said $\lambda_i$;

a container through which said chemical mixture passes, said container being transparent to said $\lambda_i$;

a means for directing said incident beam at said container through which said incident beam passes as a transported beam;

means for measuring each of said $I_0(\lambda_i)$;

means for measuring an intensity $I(\lambda_i)$ of said transported beam at each of said $\lambda_i$;

means for comparing $I_0(\lambda_i)$ and $I(\lambda_i)$ for each of said $\lambda_i$ to determine each of said $C_{i,k,l}$;

means for assigning a probability to each of said sets of relative concentrations for an initial one of said samples;

means for assigning a transition probability for a transition from each of said sets of one of said ordered samples to each of said sets on the next ordered sample;

means for accumulating said transition probability assigned to each of said sets including said transition probabilities of all transitions from a set in said initial sample;

means for choosing, for each of said sets having more than one of said transitions, the transition resulting its the highest probability for said set and discarding all other transitions;

means for generating a profile of at least one of said concentrations versus said samples.

17. A method for use on a computer for determining the most probable profile for concentrations of component chemical constituents in a chemical combination over a plurality of ordered samples of said chemical combination wherein there is a plurality set of concentrations for each of said samples comprising:

storing said plurality of sets of relative concentrations in a first storage location in said computer:

assigning a probability and storing said probability in a second storage location in said computer to each of said sets of concentrations for an initial one of said samples;

assigning a transition probability and storing said transition probability in a third storage location in said computer for a transition from each of said sets of one of said ordered samples to each of said sets of the next ordered sample;

accumulating said transition probability stored in said third storage location, assigned to each of said sets including said transition probabilities for all transitions from a set in said initial sample stored in said second storage location; and choosing, for each of said sets having more than one of said transitions, the transition resulting in the highest probability for said set and discarding all other transitions.

18. A method according to claim 17 further including a means for determining concentrations, $X_j$ of N component chemical constituents wherein j=1 to N in each sample of said chemical combinations.

19. A method according to claim 18 further including means for measuring relative spectral intensities $C_{i,k}$ for the kth ordered sample of said chemical combination at wavelength $\lambda_i$ for i=1 to M.

20. A method according to claim 19, further including means for storing relative spectral intensities $A_{ij}$ of said N component chemical constituents.

21. A method according to claim 20 wherein said $X_j$ each of said samples is determined from said relative spectral intensities $C_{i,k}$ and said relative spectral intensities $A_{ij}$.

22. A method according to claim 21, wherein said relative spectral intensities $A_{ij}$ and $C_{i,k}$ are absorbance intensities.

23. A method according to claim 21, further including said means for providing said relative spectral intensities $C_{i,k}$ is an absorbance spectrometer.

24. A method according to claim 21, wherein said relative spectral intensities $A_{ij}$ are determined using an absorbance spectrometer.

25. A method according to claim 21, wherein said means for determining is a digital computer.

26. A method according to claim 25, wherein said relative spectral intensities $A_{ij}$ are stored in said digital computer.

27. A method according to claim 21, wherein if a particular $X_j$ is determined to be less than zero, said particular $X_j$ is set equal to zero.

28. A method according to claim 21, further including a means for generating said relative spectral intensities $C_{i,k}$ at a plurality of periodic intervals in time.

29. A method according to claim 21, wherein said interval of time is less than a millisecond.

30. A method according to claim 21, wherein said chemical combination is selected from the group consisting of a solid, a liquid and a gas.

31. A method according to claim 28, wherein said combination combination is a solid, and further including a means for removing a portion of material at a surface of said solid, said ordered samples of said chemical combination being said portions at each of said plurality of periodic time intervals, each of said plurality of said periodic time intervals corresponding to a depth into said surface.

32. A method for determining the most probable profile for concentrations $X_{j,k,l}$ of N component chemical constituents, wherein j=1 to N, in a chemical combination over a plurality of K ordered samples, wherein k=1 to K of said chemical combination wherein there are L sets of relative concentrations, where l=1 to L and l>1 for each of said samples using predetermined relative spectral intensities $A_{ij}$ of said N component chemical constituents at wavelength $\lambda_i$ wherein i=1 to M, M>N comprising:

providing relative spectral intensities $C_{i,k,l}$ of said chemical combination at wavelengths $\lambda_i$, said relative concentrations $X_{j,k,l}$ from said relative spectral intensities $C_{i,k,l}$ and said relative spectral intensities $A_{ij}$, providing an electromagnetic radiation source for generating an incident beam containing said $\lambda_i$, said beam having an intensity $I_0$ at each of said $\lambda_i$;

passing said chemical combination through a container, said container transparent to said $\lambda_i$;

directing said incident beam at said container through which said beam passes as a transported beam;

measuring each of said $I_0(\lambda_i)$;

means for measuring an intensity $I(\lambda_i)$ of said transported beam at each of said $\lambda_i$ comparing $I_0(\lambda_i)$ an $I(\lambda_i)$ for each of said $\lambda_i$ to determine each of said $C_{i,k,l}$ assigning a probability to each or said sets of concentrations for an initial one of said samples;

assigning a transition probability for a transition from each of said sets of one of said ordered sample to each of said sets on the next ordered sample;

accumulating said transition probability assigned to each of said sets including said transition probabilities of all transitions from a set in said initial sample;

choosing, for each of said sets having more than one of said transition, the transition resulting in the highest probability for said set and discarding all other transitions;

generating a profile of at least one of said relative concentrations versus said samples.

33. An apparatus according to claim 1, further including:

means for determining concentrations $X_j$ of N component chemical constituents, wherein j=1 to N, in a chemical combination using predetermined relative constituent spectral intensities $A_{ij}$ of said N component chemical constituents, wherein i=1 to M, wherein M>N;

means for measuring relative spectral intensities $C_i$ of said chemical combination at wavelengths $\lambda_i$;

means for storing said $C_i$ as stored relative spectral intensities;

means for storing said $A_{ij}$ as stored predetermined relative constituent spectral intensities;

means for determining said concentrations $X_j$ said stored relative spectral intensities and said stored relative constituent spectral intensities;

means for generating a set of M surfaces each of N−1 dimensions within a region defined by $0 \leq X_j$ for j=1 to N from a set of M equations $$0 = \sum_{j=1}^{N} A_{i,j}X_j - C_i \text{ for } i = 1 \text{ to } M$$

means for determining a set of intersections of said M surfaces within said region;

means for assigning an error indicating how good said intersection is for said value of said concentrations;

means for storing said error;

means for determining which of said intersection has a minimum value of said error, said intersection having said minimum error defining said concentrations $X_j$ of said N component chemical constituents of said chemical mixture.

34. A method according to claim 17, further including the steps of:

determining the concentrations $X_j$ of N component chemical constituents, wherein j=1 to N, in a chemical combination using predetermined relative constituent spectral intensities $A_{ij}$ of said N component chemical constituents, wherein i=1 to M, wherein M>N;

measuring relative spectral intensities $C_i$ of said chemical combination at wavelengths $\lambda_i$;

storing said $C_i$ as stored relative spectral intensities;

storing said $A_{ij}$ as stored predetermined relative constituent spectral intensities;

generating a set of M surfaces each of N−1 dimensions within a region defined by $0 \leq X_i$ for i=1 to N from a set of M equations $$0 = \sum_{j=1}^{N} A_{i,j}X_j - C_i \text{ for } i = 1 \text{ to } M$$

determining a set of intersections of said M surfaces within said region;

means for assigning an error to each of said intersections indicating how good said intersection is for said value of said relative concentrations;

means for storing said error;

determining which of said intersections has a minimum value of said error, said intersection having said minimum error defining said relative concentrations $X_j$ of said N component chemical constituents of said chemical combination.

35. An apparatus according to claim 2, wherein said concentrations $X_j$ are selected from the group consisting of absolute and relative concentrations.

36. A method according to claim 18 wherein said concentrations $X_j$ are selected from the group consisting of absolute and relative concentrations.

37. A method according to claim 17 wherein said chemical combination is a chemical mixture.

* * * * *